United States Patent
Gross et al.

(10) Patent No.: US 10,551,970 B2
(45) Date of Patent: Feb. 4, 2020

(54) SYSTEM AND METHOD FOR DETECTING IMPERFECTIONS IN A SCREEN

(71) Applicant: ESW Holdings, Inc., Austin, TX (US)

(72) Inventors: Amit Gross, Kfar-Saba (IL); Oded Rozenberg, Modiin (IL); Moshe Lipsker, Moshav Nehusha (IL)

(73) Assignee: ESW Holdings, Inc., Austin, TX (US)

(*) Notice: Subject to any disclaimer, the term of this patent is extended or adjusted under 35 U.S.C. 154(b) by 0 days.

(21) Appl. No.: 15/867,771

(22) Filed: Jan. 11, 2018

(65) Prior Publication Data
US 2019/0212872 A1    Jul. 11, 2019

(51) Int. Cl.
*G06F 3/041* (2006.01)
*G01N 29/12* (2006.01)
*G01N 29/46* (2006.01)
*G06F 3/0488* (2013.01)

(52) U.S. Cl.
CPC .......... *G06F 3/0418* (2013.01); *G01N 29/12* (2013.01); *G01N 29/46* (2013.01); *G06F 3/04883* (2013.01)

(58) Field of Classification Search
CPC ........ G06F 3/043; G06F 3/0433; G06F 3/041; G06F 2203/04104; G06F 3/0418; G06F 3/04883; G06F 3/044; G06F 3/1423; G06F 2203/04106; G06F 3/016
See application file for complete search history.

(56) References Cited

U.S. PATENT DOCUMENTS

| | | | |
|---|---|---|---|
| 2005/0102109 A1* | 5/2005 | Dubois | G01N 29/0645 702/39 |
| 2013/0093732 A1* | 4/2013 | Esteve | G06F 1/169 345/177 |
| 2016/0209980 A1* | 7/2016 | Funston | G06F 3/0416 |
| 2017/0003872 A1* | 1/2017 | Dash | G06F 3/04886 |
| 2017/0315007 A1* | 11/2017 | Fitzgerald | G01L 5/22 |
| 2018/0268783 A1* | 9/2018 | Woo | G09G 5/373 |

* cited by examiner

*Primary Examiner* — Md Saiful A Siddiqui

(57) ABSTRACT

A method and system for detecting imperfections on a surface of a touchscreen of an electrical device, comprising: swiping a test object, such as a fingertip, a fingernail or a pin, along at least a portion of the touchscreen; producing, by the touchscreen, an electric signal indicative of the test object's contact with the touchscreen; receiving an acoustic signal by an acoustic sensor, during the swipe of the test object along the touchscreen; analyzing, by a processor, at least one of the electric signal and received acoustic signal; and determining existence of imperfections on the touchscreen's surface based on the analysis.

20 Claims, 7 Drawing Sheets

--- s1005: swiping a test object along at least a portion of the touchscreen s1010: producing, by the touchscreen, an electric signal indicative of the test object's contact with the touchscreen s1015: receiving an acoustic signal by an acoustic sensor, during the swipe of the test object along the touchscreen s1020: analyzing, by a processor, at least one of the electric signal and acoustic signal s1025: determining existence of imperfections on the touchscreen's surface based on the analysis.

s1005: swiping a test object along at least a portion of the touchscreen s1010: producing, by the touchscreen, an electric signal indicative of the test object's contact with the touchscreen s1015: receiving an acoustic signal by an acoustic sensor, during the swipe of the test object along the touchscreen s1020: analyzing, by a processor, at least one of the electric signal and acoustic signal s1025: determining existence of imperfections on the touchscreen's surface based on the analysis.

Figure 4 ns of the present invention provide a method of detecting imperfections on a surface of a touchscreen of an electrical device, comprising: swiping a test object along at least a portion of the touchscreen; producing, by the touchscreen, an electric signal indicative of the test object's contact with the touchscreen; receiving an acoustic signal by an acoustic sensor, during the swipe of the test object along the touchscreen; analyzing, by a processor, at least one of the electric signal and received acoustic signal; and determining existence of imperfections on the touchscreen's surface based on the analysis.

SYSTEM AND METHOD FOR DETECTING IMPERFECTIONS IN A SCREEN

FIELD OF THE INVENTION

The present invention relates to detection of imperfections in screens. More particularly, the present invention relates to systems and methods for remote detection of imperfections in touchscreens.

BACKGROUND OF THE INVENTION

Touchscreens have become a vital and expensive component of consumer electronic devices everywhere. With the rising demand to insure, diagnose malfunctions in and refurbish electronic devices, a method for remote detection of broken screens has become an imperative demand. For example, in processing a buyback of a failed product or under a money-return guarantee, a user may be requested to indicate if the screen of the electronic device is broken or not. Such manual request from a user causes the assessment of the electric device's condition to be vulnerable to fraud and mistakes.

Some solutions for detection of cracks on a touchscreen surface currently available on the market involve taking a picture or a video sequence of the examined device, and analyzing the outcome to determine the touchscreen's condition. For example, light reflection may be analyzed to ascertain whether a touchscreen is fractured. However, the presently available methods require dedicated hardware (e.g.: a proprietary camera) as well as strict standardization, (e.g.: alignment of the device, distance from the camera, lighting and cleaning of the screen due to light reflecting marks). These requirements render the available methods inaccurate, and susceptible to errors.

SUMMARY OF THE INVENTION

There is thus provided, in accordance with some embodiments of the invention, a method and system for detecting imperfections in a screen.

Embodiments of the present invention provide a method of detecting imperfections on a surface of a touchscreen of an electrical device, comprising: swiping a test object along at least a portion of the touchscreen; producing, by the touchscreen, an electric signal indicative of the test object's contact with the touchscreen; receiving an acoustic signal by an acoustic sensor, during the swipe of the test object along the touchscreen; analyzing, by a processor, at least one of the electric signal and received acoustic signal; and determining existence of imperfections on the touchscreen's surface based on the analysis.

Some embodiments may further include analyzing by the processor, the electric signal, indicative of the test object's contact with the touchscreen, to detect the circumference of the test object's contact area with the touchscreen.

Other embodiments may further include: defining at least one requirement for the circumference of the test object's contact area with the touchscreen; and if the requirement is not met, prompting a user to apply changes to the test object to meet the defined requirement.

In some embodiments, the method may further include: presenting a pattern on the touchscreen and prompting a user to swipe a test object along the presented pattern; analyzing the electric signal, indicative of the test object's contact with the touchscreen; verifying follow of the test object's swipe along the presented pattern, based on the analysis; and prompting the user to repeat the swipe along at least a portion of the presented pattern, if the verification has failed.

The method, according to some embodiments, may further include: detecting whether a screen cover is applied to the touchscreen, based on analysis of data received from one or more sensors of the electrical device; and prompting a user to remove the cover and repeat the swipe if a screen cover has been detected.

According to some embodiments, determining the existence of imperfections based on the analysis may further include: extracting values of at least one parameter of the acoustic signal; and determining existence of imperfections if the extracted values are within at least one predetermined range.

According to some embodiments, analysis of the electric signal may further include: forming an initial group of labeled touchscreens, comprising at least one touchscreen with at least one known imperfection, and at least one touchscreen without imperfections; extracting at least one feature from the electric signal relating to each touchscreen of the initial group of labeled touchscreens; classifying each touchscreen of the labeled group of touchscreens to classes according to said at least one feature, wherein each class is associated with touchscreens having or not having imperfections; producing an additional electric signal, from an additional unlabeled touchscreen; extracting the at least one feature from the additional electric signal of the additional unlabeled touchscreen; and associating the additional touchscreen with a class of touchscreens having or not having imperfections.

According to some embodiments, analysis of the acoustic signal may further include: forming an initial group of labeled touchscreens, comprising at least one touchscreen with at least one known imperfection, and at least one touchscreen without imperfections; extracting at least one feature from the acoustic signal relating to each touchscreen of the initial group of labeled touchscreens; classifying each touchscreen of the labeled group of touchscreens to classes according to said at least one feature, wherein each class is associated with touchscreens having or not having imperfections; receiving an additional acoustic signal, from an additional unlabeled touchscreen; extracting the at least one feature from the additional acoustic signal of the additional unlabeled touchscreen; and associating the additional touchscreen with a class of touchscreens having or not having imperfections.

According to one embodiment, the extracted feature may include at least one of: frequencies, amplitudes, Fast Fourier Transform (FFT) coefficients, Discrete Fourier Transform (DFT) coefficients, Discrete Cosine Transform (DCT) coefficients, Discrete Wavelet Transform (DWT) coefficients, and Mel-Frequency Cepstral Coefficients (MFCC).

According to some embodiments, the electric device is one of a smartphone, a personal digital assistant (PDA), a tablet computer, an e-reader, a laptop, a computer screen, a television screen, a game console, and a point-of-sale (POS) screen.

According to some embodiments the acoustic sensor is associated with the electric device, and is one of a microphone and a piezoelectric sensor.

A system for detecting imperfections on a surface of a touchscreen of an electrical device, according to some embodiments, may include: at least one non-transitory memory device, wherein at least one module of instruction code is stored; at least one processor associated with the at least one non-transitory memory device. According to some embodiments, the at least one processor may be configured upon execution of the at least one module of instruction code to: receive an electric signal produced by the touchscreen, indicative of a test object's contact with the touchscreen; receive an acoustic signal produced by an acoustic sensor, during a swipe of the test object along the touchscreen; analyze at least one of the electric signal and acoustic signal; and determine existence of imperfections on the touchscreen's surface based on the analysis.

According to some embodiments, the at least one processor is further configured to analyze the electric signal indicative of the test object's contact with the touchscreen, and detect the circumference of the test object's contact area with the touchscreen.

According to some embodiments, the at least one processor may be further configured to receive at least one requirement for the circumference of the test object's contact area with the touchscreen; and if the requirement is not met, prompt a user to apply changes to the test object to meet the received at least one requirement.

In yet other embodiments, the at least one processor may be further configured to: present a pattern on the touchscreen and prompt a user to swipe a test object along the presented pattern; analyze the electric signal, indicative of the test object's contact with the touchscreen; verify follow of the test object's swipe along the presented pattern, based on the analysis; and prompt the user to repeat the swipe along at least a portion of the presented pattern, if the verification has failed. The at least one processor may further be configured to: detect whether a screen cover is applied to the touchscreen, based on analysis of data received from one or more sensors of the electrical device; and prompt the user to remove the cover and repeat the swipe if a screen cover has been detected.

According to some embodiments, the at least one processor may be configured to determine the existence of imperfections based on the analysis by: extracting values of at least one parameter of the acoustic signal; and determining existence of imperfections if the extracted values are within at least one predetermined range.

According to some embodiments, the analysis of the electric signal by the at least one processor may further comprise: forming an initial group of labeled touchscreens, comprising at least one touchscreen with at least one known imperfection, and at least one touchscreen without imperfections; extracting at least one feature from the electric signal relating to each touchscreen of the initial group of labeled touchscreens; classifying each touchscreen of the labeled group of touchscreens to classes according to said at least one feature, wherein each class is associated with touchscreens having or not having imperfections; producing an additional electric signal, from an additional unlabeled touchscreen; extracting the at least one feature from the additional electric signal of the additional unlabeled touchscreen; and associating the additional touchscreen with a class of touchscreens having or not having imperfections. In yet other embodiments, analysis of the acoustic signal by the at least one processor may further comprise: forming an initial group of labeled touchscreens, comprising at least one touchscreen with at least one known imperfection, and at least one touchscreen without imperfections; extracting at least one feature from the acoustic signal relating to each touchscreen of the initial group of labeled touchscreens; classifying each touchscreen of the labeled group of touchscreens to classes according to said at least one feature, wherein each class is associated with touchscreens having or not having imperfections; receiving an additional acoustic signal, from an additional unlabeled touchscreen; extracting the at least one feature from the additional acoustic signal of the additional unlabeled touchscreen; and associating the additional touchscreen with a class of touchscreens having or not having imperfections.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4 is a flow diagram depicting a method of implementing a touch test, according to some embodiments;

Figure 1:
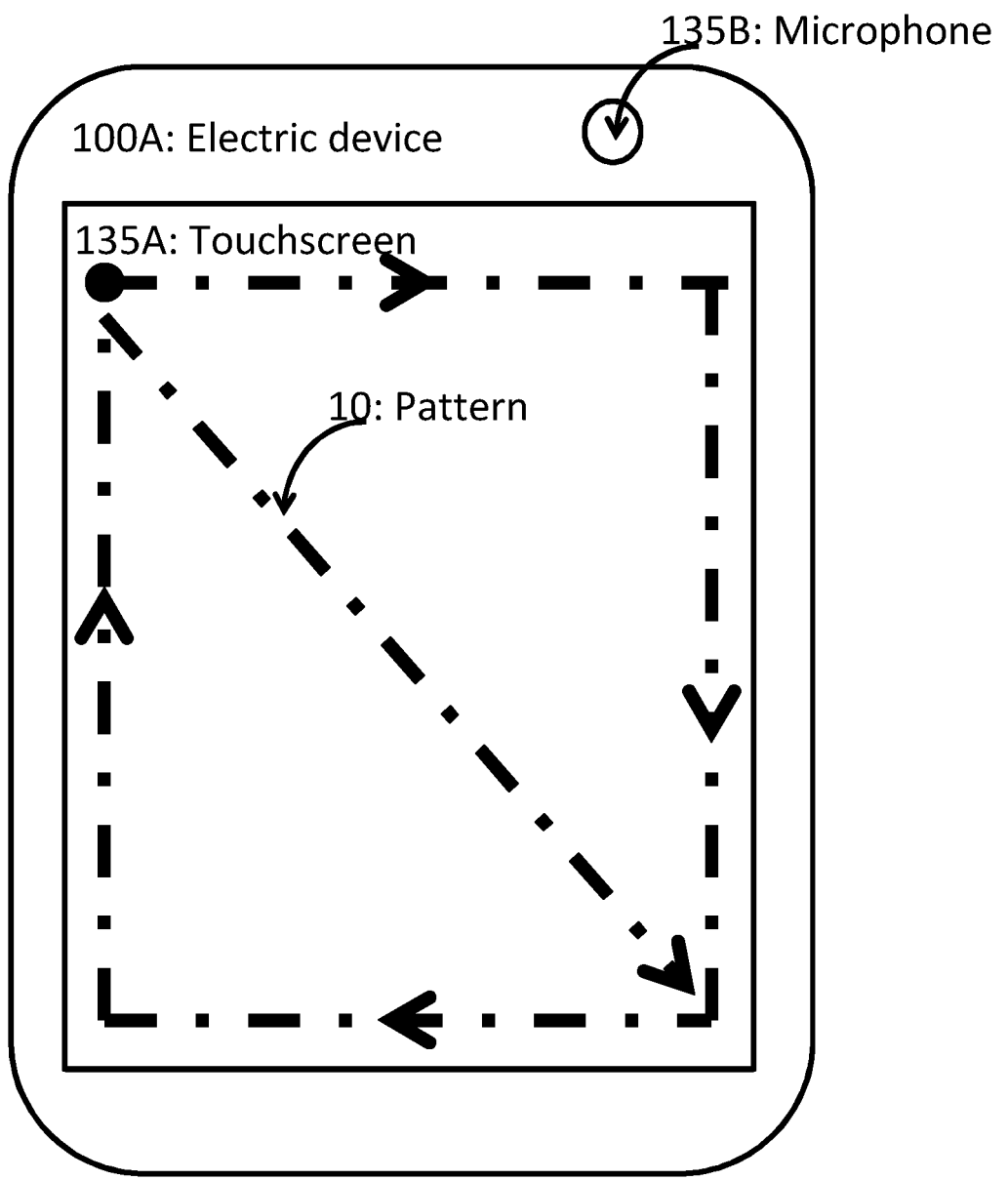
FIG. 1 is a block diagram, depicting an electric device according to some embodiments.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Embodiments of the present invention disclose a method and a system for performing a touch test, to analyze the condition of a touchscreen embedded within an electric device. The term "condition of the touchscreen" henceforth relates to existence of imperfections on the touchscreen's surface, such as cracks, scratches, fractures, dents and holes, or the absence thereof. The term "touch test" henceforth relates to a test procedure, performed by a user on a specific touchscreen, involving touching the touchscreen with a test object, to ascertain the condition of the touchscreen, as elaborated further below.

According to some embodiments, the method includes at least part of the steps of: prompting a user to swipe a test object along a touchscreen; producing an electric signal by the touchscreen, indicative of the test object's contact with the touchscreen; recording the electric signals produced by the touchscreen; sensing an audio signal produced by the swiping of the test object across the touchscreen by an audio sensor; recording the audio signal received by the audio sensor; recording electrical signals that are produced by the audio sensor consequent to the reception of the audio signals; and analyzing the recorded audio signal and/or electric signals by a processor, to determine whether the test object has encountered imperfections on the touchscreen's surface.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently. As used herein, the term "follow" may be used as a noun to denote correspondence of a sensed pattern or shape with a predetermined pattern or shape. "Audio sensor" is used interchangeably herein with "acoustic sensor" to refer to an audio or acoustic sensor, such as a microphone or piezoelectric transducer, and an "audio signal" or "acoustic signal' refers to a signal generated by such device.

Reference is now made to FIG. 1 which depicts a schematic illustration of an electric device 100A according to some embodiments. In this embodiment, electric device 100A may include a touchscreen 135A and a microphone 135b, and may be any of: a smartphone, a personal digital assistant (PDA), a tablet, an e-reader, a laptop, a computer screen, a television screen, a game console, a point-of-sale (POS) screen, and the like.

According to some embodiments, the electric device 100A of FIG. 1 may be a computing device (e.g.: device 100 in FIG. 2), as elaborated further below.

The electric device 100A of FIG. 1 is configured to present a pattern 10 on the touchscreen, and prompt a user to perform a touch test, to detect imperfections (e.g. cracks, holes, and the like) in the surface of the touchscreen, as elaborated further below.

Figure 2:
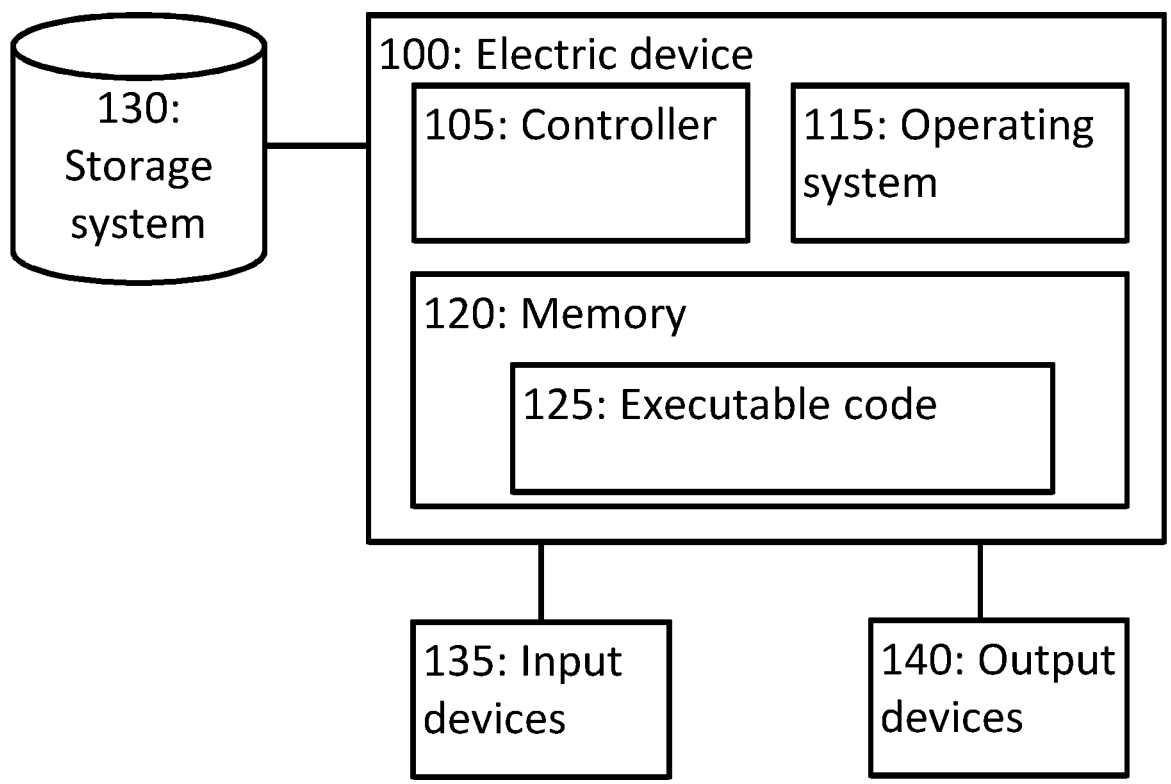
FIG. 2 depicts a schematic illustration of an electrical device, including a touchscreen and a microphone, and configured to perform a touch test, according to some embodiments.

Reference is now made to FIG. 2, depicting a block diagram of a computing device 100, according to some embodiments. Computing device 100 may include a controller 105 that may be, for example, a central processing unit processor (CPU), a chip or any suitable computing or computational device, an operating system 115, a memory 120, executable code 125, a storage system 130 that may include, input devices 135 and output devices 140. Controller 105 (or one or more controllers or processors, possibly across multiple units or devices) may be configured to carry out methods described herein, and/or to execute or act as the various modules, units, etc. More than one computing device 100 may be included in, and one or more computing devices 100 may act as the components of, a system according to embodiments of the invention.

Operating system 115 may be or may include any code segment (e.g., one similar to executable code 125 described herein) designed and/or configured to perform tasks involving coordination, scheduling, arbitration, supervising, controlling or otherwise managing operation of computing device 100, for example, scheduling execution of software programs or tasks or enabling software programs or other modules or units to communicate. Operating system 115 may be a commercial operating system. It will be noted that an operating system 115 may be an optional component, e.g., in some embodiments, a system may include a computing device that does not require or include an operating system 115.

Memory 120 may be or may include, for example, a Random-Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short-term memory unit, a long-term memory unit, or other suitable memory units or storage units. Memory 120 may be or may include a plurality of, possibly different memory units. Memory 120 may be a computer or processor non-transitory readable medium, or a computer non-transitory storage medium, e.g., a RAM.

Executable code 125 may be any executable code, e.g., an application, a program, a process, task or script. Executable code 125 may be executed by controller 105 possibly under control of operating system 115. For example, executable code 125 may be an application that enforces security in a vehicle as further described herein. Although, for the sake of clarity, a single item of executable code 125 is shown in FIG. 2, a system according to some embodiments of the invention may include a plurality of executable code segments similar to executable code 125 that may be loaded into memory 120 and cause controller 105 to carry out methods described herein.

Storage system 130 may be or may include, for example, a flash memory as known in the art, a memory that is internal to, or embedded in, a micro controller or chip as known in the art, a hard disk drive, a CD-Recordable (CD-R) drive, a Blu-ray disk (BD), a universal serial bus (USB) device or other suitable removable and/or fixed storage unit. Content may be stored in storage system 130 and may be loaded from storage system 130 into memory 120 where it may be processed by controller 105. In some embodiments, some of the components shown in FIG. 2 may be omitted. For example, memory 120 may be a non-volatile memory having the storage capacity of storage system 130. Accordingly, although shown as a separate component, storage system 130 may be embedded or included in memory 120. Model 136 may be, or may include, a timing model that includes timing properties of messages, or expected behavior of messages, as described herein. As further described, model 136 may be, or may include, a content model that may include content attributes or properties of messages, or expected content related behavior of messages, as described herein.

Input devices 135 may be or may include any suitable input devices, components or systems, e.g., a detachable keyboard or keypad, a mouse and the like. Output devices 140 may include one or more (possibly detachable) displays or monitors, speakers and/or any other suitable output devices. Any applicable input/output (I/O) devices may be connected to computing device 100 as shown by blocks 135 and 140. For example, a wired or wireless network interface card (NIC), a universal serial bus (USB) device or external hard drive may be included in input devices 135 and/or output devices 140. It will be recognized that any suitable number of input devices 135 and output device 140 may be operatively connected to computing device 100 as shown by blocks 135 and 140.

A system according to some embodiments of the invention may include components such as, but not limited to, a plurality of central processing units (CPU) or any other suitable multi-purpose or specific processors or controllers (e.g., controllers similar to controller 105), a plurality of input units, a plurality of output units, a plurality of memory units, and a plurality of storage units.

Figure 3:
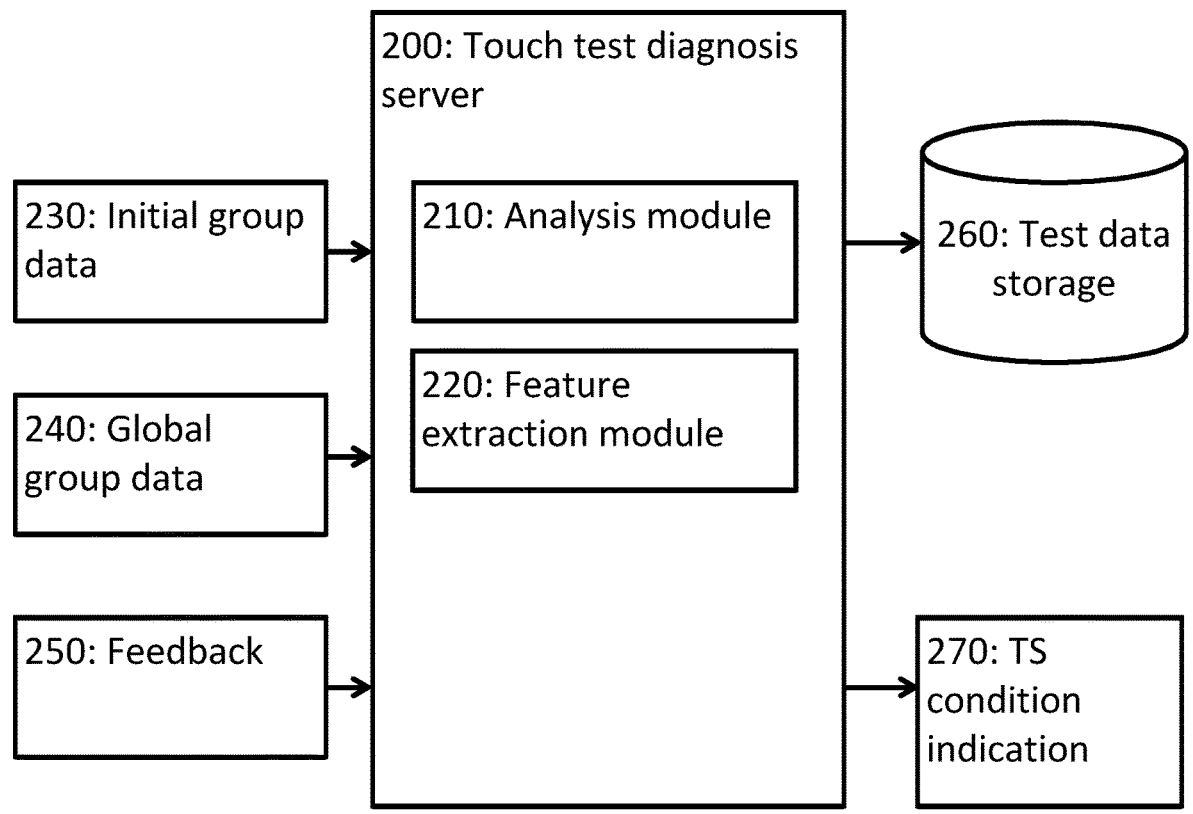
FIG. 3 is a block diagram of a diagnosis server, according to some embodiments.

Reference is now made to FIG. 3, which is a block diagram of a touch test diagnosis server 200, according to some embodiments.

According to some embodiments, the diagnosis server 200 may be implemented on the same device as the electric device (e.g.: device 100A of FIG. 1) upon which the touch test is performed. According to other embodiments, the diagnosis server 200 may be implemented on another device, (for example on computing device 100 of FIG. 2), different from the device upon which the touch test is performed.

According to some embodiments, the touch test diagnosis server may be configured to receive data 230, 240, 250 from at least one electric device (e.g.: element 100A in FIG. 1), pertaining to a touch test that has been performed on the touchscreen of the electric device (e.g.: element 135A in FIG. 1).

According to some embodiments, the data received from the at least one electric device may include at least one of: an audio signal, produced during swiping of the test object along the touchscreen; an electric signal, produced by the touchscreen, indicative of a test object's contact with the touchscreen; acquired by an acoustic sensor such as a microphone (e.g.: microphone 135B in FIG. 1) or a piezo-electric sensor.

According to some embodiments, the data received from the at least one electric device may include data from one or more sensors of the electrical device, such as, for example a proximity sensor, a pressure sensor, barometer sensor and the like.

According to some embodiments, when the diagnosis server 100 is implemented on a device other than the electric device (e.g. 100A of FIG. 1) on which the touch test is performed, the diagnosis server 100 may receive the data during the touch test, and present indications to a user, for controlling the flow of the touch test. For example, the diagnosis server 100 may receive the electric signal, indicative of a test object's contact with the touchscreen, and indicate whether values of properties expressed by the electrical signal are within a predefined range. Such properties may include, for example: circumference of the contact area of the test object with the touchscreen, location of the test object's contact with the touchscreen, and amplitude of the electric signal. For example, if a circumference of the contact area of the test object with the touchscreen does not meet predefined conditions, the user may be presented a requirement to use a different test object, so as to meet the predefined conditions.

According to other embodiments, the electric device (e.g. element 100 of FIG. 1) may be configured to emit indications for controlling the flow of the touch test according to properties, such as the aforementioned properties, whereas the diagnosis server 100 may perform the analysis of data, to determine the condition of the touchscreen.

According to other embodiments where the diagnosis server 100 and the electric device (e.g. element 100 of FIG. 1) are implemented on the same device, both the indications for controlling the flow of the touch test and analysis of data are performed on the same device.

According to some embodiments, the diagnosis server 100 may receive data pertaining to an initial group 230 of touchscreens, comprising at least one touchscreen with at least one imperfection, and at least one touchscreen without imperfections, and data pertaining to a global group 240 of touchscreens, from beyond the initial group of touchscreens.

The diagnosis server 100 may further receive feedback data from an external source (e.g.: a user interface and/or a database), to facilitate differentiation between touchscreens with and without imperfections. The feedback data may include, for example, at least one of: values of parameters pertaining to the audio signal; values of parameters pertaining to the electric signal; values of parameters pertaining to various sensors associated with the electric device; predetermined ranges of the parameters for determining existence of imperfections; predetermined ranges of the parameters for determining existence of a screen cover; general information regarding specific touchscreens (e.g.: type of touchscreen, type of electric device associated with the touchscreen); and information regarding the condition of specific touchscreens (e.g.: existence, of imperfections, type of imperfections and location of imperfections on the touchscreen).

According to some embodiments, the diagnosis server 100 may include a feature extraction module 220, configured to extract features of data from at least one of the audio signal and electric signal. The extracted features may include at least part of: value of parameters pertaining to at least one of the audio signal and electric signal (e.g.: duration, frequency, amplitude and the like); statistical information (e.g.: correlation between the signals, correlation between portions of the signals, cross-correlation between the signals, and the like) and products of computational transformations applied to at least one of the audio signal and electric signal. Examples for such products of computational transformations include: Fast Fourier Transform (FFT) coefficients, Discrete Fourier Transform (DFT) coefficients, Discrete Cosine Transform (DCT) coefficients, Discrete Wavelet Transform (DWT) coefficients, and Mel-Frequency Cepstral Coefficients (MFCC) and the like.

According to some embodiments, the diagnosis server 100 may include an analysis module 210, configured to: analyze the data extracted from the feature extraction module 220; and determine existence of imperfections if the extracted values are within a predetermined range.

According to some embodiments, the analysis module 210 may be configured to: analyze the data extracted from the feature extraction module 220; determine at least one difference in at least one extracted feature of at least one of the audio signal, and electric signal between a touchscreen with an imperfection and one without imperfections from an initial group of touchscreens; and utilize the determined difference to ascertain the existence of an imperfection on a touchscreen from beyond the initial group of touchscreens.

According to some embodiments, the analysis module 210 may be implemented as a supervised machine-learning (ML) model, configured to be trained by an initial training set (e.g.: the initial touchscreen group) and by input from a supervised feedback (e.g. element 250 of FIG. 3). After the ML model has been sufficiently trained, the model may be utilized to predict (e.g.: to determine) whether additional data pertaining to a touchscreen from a global group of touchscreens 240 (e.g., beyond the initial group of touchscreens) indicates a touchscreen with or without imperfections. According to some embodiments, the machine-learning (ML) model may be of any type known in the art for supervised classification, and/or unsupervised clustering of acoustic and/or electric signal features, including for example Convolutional Neural Networks, Support Vector Machines (SVMs), K-Means clustering, or any other type of supervised or unsupervised ML model known in the art.

According to some embodiments, the analysis module 210 may be configured to form, and/or receive an initial group of labeled touchscreens, comprising at least one touchscreen that has at least one known imperfection, and at least one touchscreen without imperfections. According to some embodiments, the labeling of each touchscreen in the initial group may be received by a user, or via an initial group data module (e.g. element 230 of FIG. 3).

According to some embodiments, the analysis module 210 may be configured to obtain at least one feature from the feature extraction module 220, pertaining to at least one of the acoustic signal and electric signal, and relating to each touchscreen of the initial group of labeled touchscreens.

According to some embodiments, the analysis module 210 may be configured to classify each touchscreen of the labeled group of touchscreens to classes according to the feature obtained from the feature extraction module. Each such class may be associated with touchscreens that have or do not have imperfections. According to some embodiments, each class may also be associated with at least one specific parameter relating to the imperfection, including for example a type (e.g.: a fracture, scratch or hole), location (e.g., at the middle or at the circumference of the touchscreen), and the like.

According to some embodiments, the analysis module 210 may be configured to receive an additional acoustic signal from an additional unlabeled touchscreen, and at least one feature extracted from the additional acoustic signal of the additional unlabeled touchscreen, and associate the additional touchscreen with a class of touchscreens, to determine whether the additional touchscreen does or does not have imperfections, and parameters of determined imperfections.

According to some embodiments, the diagnosis server 200 may present the determined condition of a specific touchscreen via a condition indication module 270. The condition indication module may, for example, be configured to present the examined touchscreen's condition on a dedicated display, or transmit the result of the analysis performed by the analysis module 210 to a user, a third party, such as a maintenance service provider, an insurer, and the like. The result may be transmitted via a wired or wireless communication.

According to some embodiments, the diagnosis server 200 may be configured to store information relating to specific touch tests on a test data storage module 260. The information may, for example serve to: enhance future analysis of touch tests; and record the condition of specific, diagnosed touchscreens.

Reference is now made to FIG. 4, which depicts a flow diagram of a method of implementing a touch test, according to some embodiments. The method may include: swiping a test object along at least a portion of the touchscreen (s1005); producing, by the touchscreen, an electric signal indicative of the test object's contact with the touchscreen (s1010); receiving an acoustic signal by an acoustic sensor, during the swipe of the test object along the touchscreen (s1015); analyzing, by a processor, at least one of the electric signal and the acoustic signal (s1020); and determining existence of imperfections on the touchscreen's surface based on the analysis (s1025).

Figure 5A:
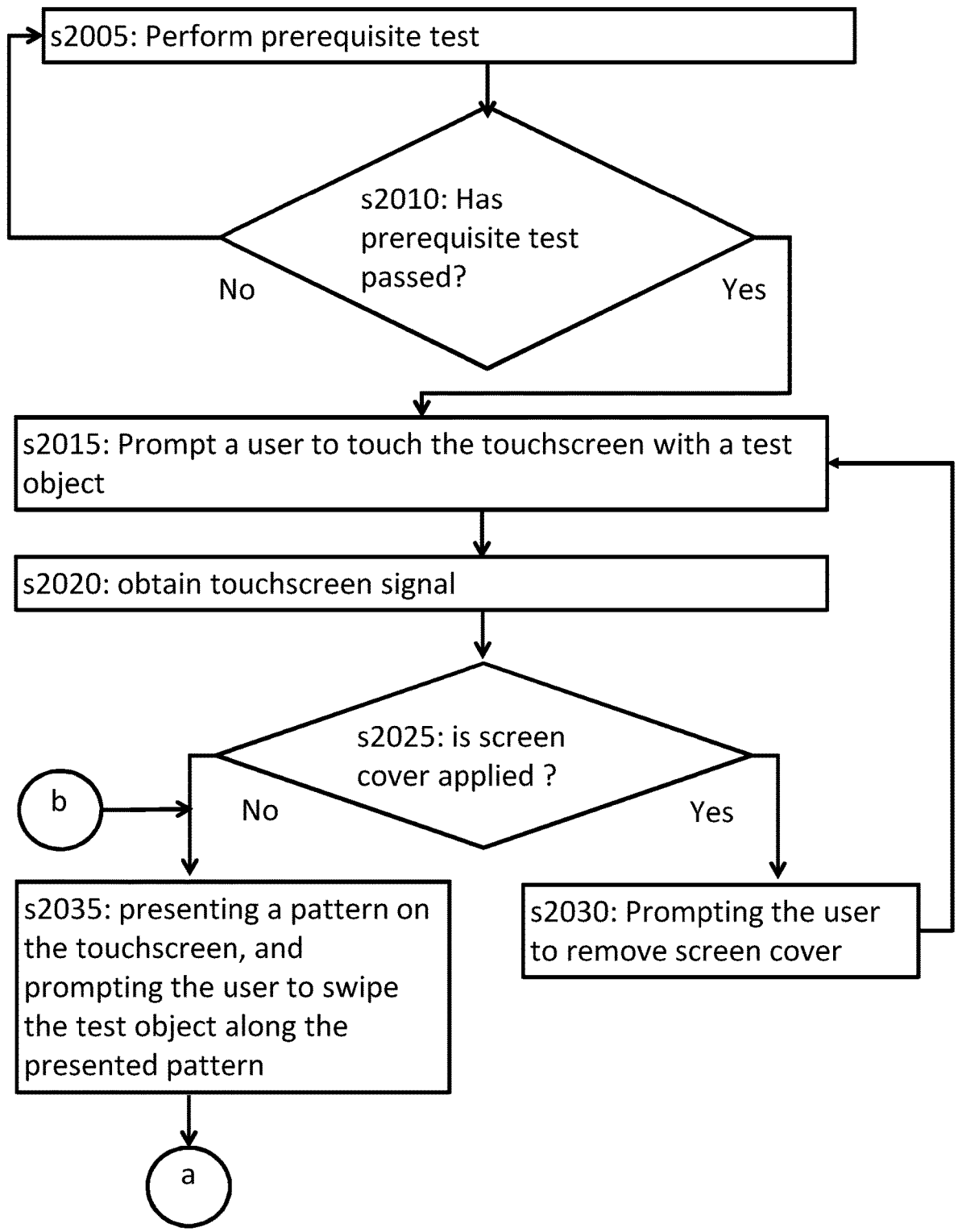
FIGS. 5A, 5B and 5C jointly comprise a flow diagram, depicting a method of implementing a touch test, according to some embodiments.
Figure 5B:
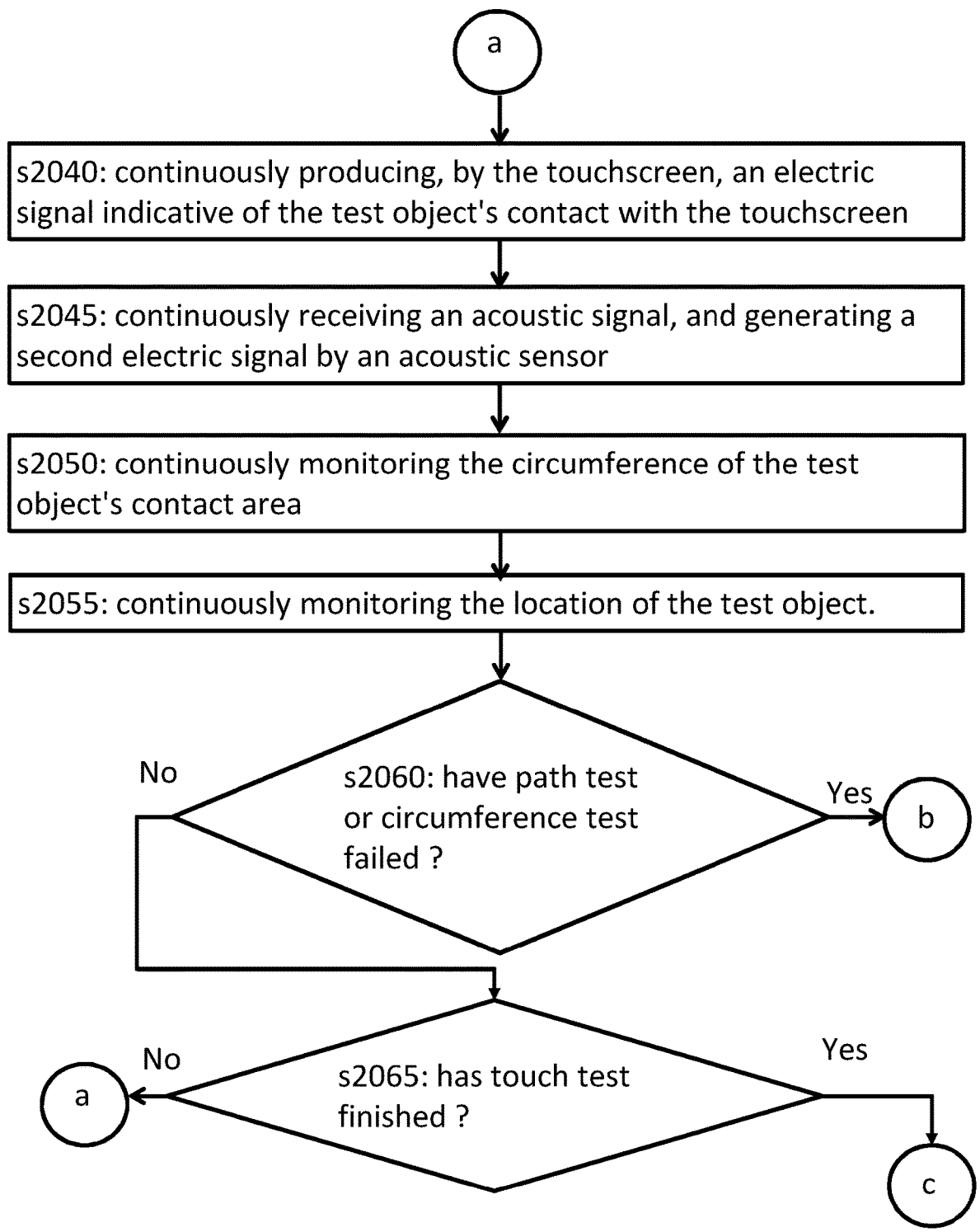
Figure 5C:
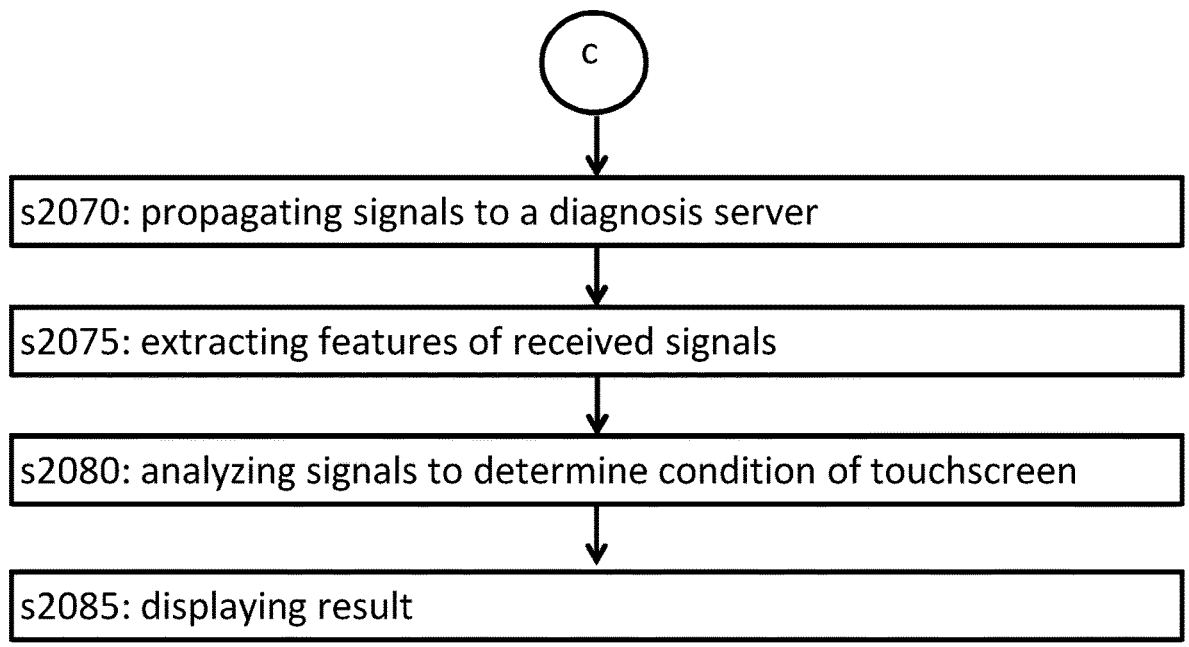

Reference is now made to FIGS. 5A, 5B and 5B, which jointly comprise a flow diagram, depicting a method of implementing a touch test, according to some embodiments.

According to some embodiments, the electric device (e.g.: a smartphone or a tablet computer, such as electric device 100A of FIG. 1), which is associated with the examined touchscreen (touchscreen 135A of FIG. 1) may run an application, to support the performance of the touch test, by monitoring electric and/or acoustic signals pertaining to the touch test, and prompting a user to act according to the monitored signals and the different stages of the touch test, as described below.

According to some embodiments, the electric device may be configured to perform at least one prerequisite test (s2005), to ascertain whether the touch test may be performed on the electric device. The at least one prerequisite test may include, for example: a self-test of an electric device's microphone (e.g. by using audio speakers associated with the electric device); a test for verifying that no earphones are plugged into a socket of the electric device; and a test for verifying that the device is not in 'mute' mode. According to some embodiments, the touch test may not be commenced before the prerequisite test has passed (s2010).

According to some embodiments, after the prerequisite test has successfully passed, the electric device may be configured to prompt a user to touch the touchscreen with a test object (s2015). According to some embodiments, the test object may be the user's fingernail, a conductive object (e.g. a pin) held by the user, or another object that has sufficient capacitance to be detected by the examined touchscreen.

According to some embodiments, the application may obtain the electric signal produced by the touchscreen in response to the contact of the test object with the touchscreen (s2020), and determine whether a screen cover is applied to the touchscreen (s2025). If so, the application may prompt the user to remove the screen cover, and to touch the screen again with the test object, to verify the screen cover's removal (s2030). If no screen cover is applied to the touchscreen's surface, the application running on the electric device may present a pattern on the touchscreen, and prompt the user to swipe the test object along the presented pattern (s2035).

According to some embodiments, as the user swipes the test object along the touchscreen's surface, the touchscreen continuously produces an electric signal indicative of the test object's contact with the touchscreen (S2040). According to some embodiments, the electric signal may indicate at least part of: the location, the area and the consistency of the test object's contact with the touchscreen's surface. According to some embodiments the electric device is configured to record the electric signal in a memory (e.g.: element 120 of FIG. 2).

According to some embodiments, the electric device is configured to continuously receive an acoustic signal, produced by the swiping of the test object along the screen, by an acoustic sensor (S2045). The acoustic sensor may, for example, be a microphone embedded within the electric device (e.g.: element 135B of FIG. 1), an external microphone, or a piezoelectric transducer associated with the electric device. According to some embodiments the electric device is configured to record the acoustic signal in a memory (e.g.: memory 120 of FIG. 2).

According to some embodiments, the circumference of the test object's contact area may be required to be such that the test object would intrude into imperfections such as cracks, scratches, or holes on the touchscreen's external surface, in a manner that is noticeable and/or measurable by electronic sensors embedded within the electric device. For example, a finger may be swiped across a cracked screen without significantly intruding into the cracks, whereas a fingernail or a pin would intrude into the cracks in a manner that is identifiable through analysis of acoustic and/or electric signals pertaining to the swiping of the pin or fingernail across the screen. According to these embodiments, the application running on the electric device may be configured to continuously perform a circumference test, where the circumference of the test object's contact area is continuously monitored, and compared with a predefined, maximal circumference threshold value (s2050).

According to some embodiments, the application may be configured to perform a path test, where the location of the test object is continuously monitored, to ensure that the user follows the swipe of the test object along the presented path (s2055). According to other embodiments, the touch test may be performed by aggregating individual swipes of the test object, and analyzing at least one of the audio signal, and electric signal pertaining to each of the individual swipes, without presenting a pattern, and without prompting the user to follow a pattern for the test object's location.

According to some embodiments, the application may be configured to determine whether the circumference test has failed (e.g.: if the circumference of the test object's contact area with the touchscreen at any moment of the touch test has exceeded the predefined maximal circumference threshold value), or if the path test has failed (e.g.: if the path of the swiped test object does not follow the presented pattern). According to some embodiments, if one of the path test or circumference test has failed (s2060), the touch test may be restarted, and the user may be prompted to restart the swipe of the test object along the presented pattern.

According to some embodiments, the application may be configured to continuously check (s2065) whether the touch test has been completed (e.g.: the test object has been swiped along the entire presented pattern). If so, then the application may be configured to propagate (s2070) at least one of the acoustic signal and electric signal to a diagnosis server (e.g.: element 200 of FIG. 3).

According to some embodiments, the feature extraction module of the diagnosis server (e.g.: element 220 of FIG. 3) is configured to extract features pertaining to at least one of the audio signal and electric signal (s2075), as discussed above in relation to FIG. 3.

According to some embodiments, the analysis module of the diagnosis server (e.g.: element 210 of FIG. 3) is configured to analyze at least one of the audio signal and electric signal (s2080), and determine whether the examined touchscreen has at least one imperfection, as discussed above in relation to FIG. 3. According to some embodiments, the diagnosis server 200 is further configured to present the result of the touch test, and indicate the condition of the touchscreen (s2085), as discussed above in relation to FIG. 3.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of detecting imperfections on a surface of a touchscreen of an electrical device, comprising:
   swiping a test object along at least a portion of the touchscreen;
   producing, by the touchscreen, an electric signal indicative of the test object's contact with the touchscreen;
   receiving an acoustic signal by an acoustic sensor, during the swipe of the test object along the touchscreen;
   analyzing, by a processor, at least one of the electric signal and received acoustic signal, wherein the analyzing includes:
      referencing an initial group of labeled touchscreens, comprising at least one touchscreen with at least one known imperfection, and at least one touchscreen without imperfections, wherein:
         at least one feature has been extracted from an electric signal relating to each touchscreen of the initial group of labeled touchscreens;
         each touchscreen of the labeled group of touchscreens has been classified to classes according to said at least one feature;
         each class is associated with touchscreens having or not having imperfections;
      producing an additional electric signal, from an additional unlabeled touchscreen;
      extracting, by a processor, the at least one feature from the additional electric signal of the additional unlabeled touchscreen; and
      associating, by a processor, the additional touchscreen with a class of touchscreens having or not having imperfections; and
   determining an existence of imperfections on the touchscreen's surface based on the analysis.

2. The method of claim 1, wherein said analyzing comprises analyzing by the processor of the electric signal, indicative of the test object's contact with the touchscreen, to detect a circumference of the test object's contact area with the touchscreen.

3. The method of claim 2, further comprising: defining at least one requirement for the circumference of the test object's contact area with the touchscreen; and when the requirement is not met, prompting a user to apply changes to the test object to meet the defined requirement.

4. The method of claim 1, further comprising:
   presenting a pattern on the touchscreen and prompting a user to swipe a test object along the presented pattern;
   analyzing, by a processor, the electric signal, indicative of the test object's contact with the touchscreen;
   verifying follow of the test object's swipe along the presented pattern, based on the analysis; and
   prompting the user to repeat the swipe along at least a portion of the presented pattern, when the verification has failed.

5. The method of claim 1, further comprising:
  detecting whether a screen cover is applied to the touchscreen, based on analysis of data received from the acoustic sensor; and
  prompting a user to remove the cover and repeat the swipe when a screen cover has been detected.

6. The method of claim 1, wherein determining the existence of imperfections based on the analysis further comprises:
  extracting, by a processor, values of at least one parameter of the acoustic signal; and
  determining existence of imperfections when the extracted values are within at least one predetermined range.

7. The method of claim 1, wherein analysis of the electric signal further comprises:
  forming the initial group of labeled touchscreens, comprising at least one touchscreen with at least one known imperfection, and at least one touchscreen without imperfections;
  extracting, by a processor, the at least one feature from the electric signal relating to each touchscreen of the initial group of labeled touchscreens; and
  classifying each touchscreen of the labeled group of touchscreens to classes according to said at least one feature, wherein each class is associated with touchscreens having or not having imperfections.

8. The method of claim 1, analysis of the accoustic signal further comprises:
  forming an initial group of labeled touchscreens, comprising at least one touchscreen with at least one known imperfection, and at least one touchscreen without imperfections;
  extracting, by a processor, at least one feature from the acoustic signal relating to each touchscreen of the initial group of labeled touchscreens;
  classifying each touchscreen of the labeled group of touchscreens to classes according to said at least one feature, wherein each class is associated with touchscreens having or not having imperfections;
  receiving an additional acoustic signal, from an additional unlabeled touchscreen;
  extracting the at least one feature from the additional acoustic signal of the additional unlabeled touchscreen; and
  associating the additional touchscreen with a class of touchscreens having or not having imperfections.

9. The method of claim 8, wherein the at least one feature includes at least one of: frequencies, amplitudes, Fast Fourier Transform (FFT) coefficients, Discrete Fourier Transform (DPT) coefficients, Discrete Cosine Transform (DCT) coefficients, Discrete Wavelet Transform (DWT) coefficients, and Mel-Frequency Cepstral Coefficients (MFCC).

10. A system for detecting imperfections on a surface of a touchscreen of an electrical device, comprising:
  at least one non-transitory memory device, wherein at least one module of instruction code is stored;
  at least one processor associated with the at least one non-transitory memory device, wherein the at least one processor is configured upon execution of the at least one module of instruction code to:
    receive an electric signal produced by the touchscreen, indicative of a test object's contact with the touchscreen;
    receive an acoustic signal produced by an acoustic sensor, during a swipe of the test object along the touchscreen;
    analyze at least one of the electric signal and acoustic signal, wherein to analyze includes to:
      reference an initial group of labeled touchscreens, comprising at least one touchscreen with at least one known imperfection, and at least one touchscreen without imperfections, wherein:
        at least one feature has been extracted from an electric signal relating to each touchscreen of the initial group of labeled touchscreens;
        each touchscreen of the labeled group of touchscreens has been classified to classes according to said at least one feature;
        each class is associated with touchscreens having or not having imperfections;
      produce an additional electric signal, from an additional unlabeled touchscreen;
      extract, by a processor, the at least one feature from the additional electric signal of the additional unlabeled touchscreen; and
      associate, by a processor, the additional touchscreen with a class of touchscreens having or not having imperfections; and
    determine existence of imperfections on the touchscreen's surface based on the analysis.

11. The system of claim 10, wherein at least one processor is that of a remote server, and wherein the analysis of at least one of the electric signal and acoustic signal and the determination of existence of imperfections is performed by the processor of the remote server.

12. The system of claim 10, wherein the at least one processor is further configured to analyze the electric signal indicative of the test object's contact with the touchscreen, and detect a circumference of the test object's contact area with the touchscreen.

13. The system of claim 12, wherein the at least one processor is further configured to receive at least one requirement for the circumference of the test object's contact area with the touchscreen; and when the requirement is not met, prompt a user to apply changes to the test object to meet the received at least one requirement.

14. The system of claim 10, wherein the at least one processor is further configured to:
  present a pattern on the touchscreen and prompt a user to swipe a test object along the presented pattern;
  analyze the electric signal, indicative of the test object's contact with the touchscreen;
  verify follow of the test object's swipe along the presented pattern, based on the analysis; and
  prompt the user to repeat the swipe along at least a portion of the presented pattern, when the verification has failed.

15. The system of claim 10, wherein the at least one processor is further configured to:
  detect whether a screen cover is applied to the touchscreen, based on analysis of data received from the acoustic sensor; and
  prompt the user to remove the cover and repeat the swipe when a screen cover has been detected.

16. The system of claim 10, wherein the at least one processor is configured to determine the existence of imperfections based on the analysis by:
  extracting values of at least one parameter of the acoustic signal; and
  determining existence of imperfections when the extracted values are within at least one predetermined range.

17. The system of claim 10, wherein analysis of the electric signal by the at least one processor further comprises:
- forming the initial group of labeled touchscreens, comprising at least one touchscreen with at least one known imperfection, and at least one touchscreen without imperfections;
- extracting the at least one feature from the electric signal relating to each touchscreen of the initial group of labeled touchscreens;
- classifying each touchscreen of the labeled group of touchscreens to classes according to said at least one feature, wherein each class is associated with touchscreens having or not having imperfections.

18. The system of claim 10, wherein analysis of the acoustic signal by the at least one processor further comprises:
- forming an initial group of labeled touchscreens, comprising at least one touchscreen with at least one known imperfection, and at least one touchscreen without imperfections;
- extracting at least one feature from the acoustic signal relating to each touchscreen of the initial group of labeled touchscreens;
- classifying each touchscreen of the labeled group of touchscreens to classes according to said at least one feature, wherein each class is associated with touchscreens having or not having imperfections;
- receiving an additional acoustic signal, from an additional unlabeled touchscreen;
- extracting the at least one feature from the additional acoustic signal of the additional unlabeled touchscreen; and
- associating the additional touchscreen with a class of touchscreens having or not having imperfections.

19. The system of claim 18, wherein the at least one feature includes at least one of: frequencies, amplitudes, Fast Fourier Transform (FFT) coefficients, Discrete Fourier Transform (DPT) coefficients, Discrete Cosine Transform (DCT) coefficients, Discrete Wavelet Transform (DWT) coefficients, and Mel-Frequency Cepstral Coefficients (MFCC).

20. The system of claim 10, wherein the acoustic sensor is associated with the electric device, and is one of a microphone and a piezoelectric sensor.

* * * * *